United States Patent [19]

Kato et al.

[11] Patent Number: 4,732,663
[45] Date of Patent: Mar. 22, 1988

[54] OXYGEN SENSOR

[75] Inventors: Nobuhide Kato, Aichi; Takao Murase, Konan, both of Japan

[73] Assignee: NGK Insulators, Ltd., Japan

[21] Appl. No.: 788,142

[22] Filed: Oct. 16, 1985

[30] Foreign Application Priority Data

Oct. 18, 1984 [JP] Japan .................. 59-220138

[51] Int. Cl.$^4$ ............................. G01N 27/46
[52] U.S. Cl. .................... 204/426; 204/427; 204/428
[58] Field of Search .................. 204/1, 5, 421–429

[56] References Cited

U.S. PATENT DOCUMENTS

| | | | |
|---|---|---|---|
| 3,784,459 | 1/1974 | Jackson | 204/423 |
| 3,785,947 | 1/1974 | Baldwin et al. | 204/422 |
| 4,040,930 | 8/1977 | Dillon | 204/426 |
| 4,061,117 | 12/1977 | Ikeura | 204/428 |
| 4,283,261 | 8/1981 | Maurer et al. | 204/428 |
| 4,323,440 | 4/1982 | Akatsuka | 204/428 |
| 4,334,974 | 6/1982 | Muller et al. | 204/425 |
| 4,383,907 | 5/1983 | Legrund et al. | 204/426 |
| 4,450,065 | 5/1984 | Yamada et al. | 204/412 |
| 4,505,807 | 3/1985 | Yamada | 204/425 |
| 4,606,807 | 8/1986 | Menden Hall | 204/427 |

Primary Examiner—T. Tung
Attorney, Agent, or Firm—Parkhurst & Oliff

[57] ABSTRACT

An oxygen sensor for determining an oxygen partial pressure of a measurement gas in a measurement-gas space, includes an elongate planar sensing element, a tubular protective device, and a retainer housing. The sensing element has an oxygen detecting portion adjacent to one longitudinal end thereof, and electrical terminal contacts adjacent to the other longitudinal end thereof. The tubular protective device accommodates therein the sensing element, and includes a first protective covering for protecting at least an end portion of the sensing element which is located within the measurement-gas space and exposed to the measurement gas and which includes the oxygen detecting portion. The tubular protective device further comprises a second protective covering for covering the remaining portion of the sensing element which is not exposed to the measurement gas. The tubular protective device is attached by the retainer housing to a partition wall defining the measurement-gas space. The elongate planar oxygen sensing element has a length of at least 40 mm as measured from the partition wall to the said other longitudinal end.

16 Claims, 20 Drawing Figures

OXYGEN SENSOR

BACKGROUND OF THE INVENTION

The present invention relates generally to an oxygen sensor for detecting the oxygen concentration of a measurement gas, especially an exhaust gas produced by an internal combustion engine. More particularly, the invention is concerned with such an oxygen sensor which has an elongate sensing element having an oxygen detecting portion at its one longitudinal end thereof and electrical terminal means at the other longitudinal end thereof, wherein the sensing element is accommodated in a tubular protective means such that the oxygen detecting portion is exposed to a measurement gas.

There has been known an oxygen sensor which detects or determines the oxygen concentration of an exhaust gas emitted from internal combustion engines, for the purpose of controlling the combustion of fuel burning conditions of the engine according to signals produced by the oxygen sensor, and thereby purifying the exhaust gas and minimizing fuel consumption of the engine. An example of such oxygen sensors uses a sensing element which comprises a body of oxygen-ion conductive solid electrolyte such as zirconium oxide doped with calcium oxide or yttrium oxide, and further comprises suitable electrodes disposed on opposite surfaces of the solid electrolyte body. In this oxygen sensor, one of the electrodes is exposed to a reference gas while the other electrode is exposed to the exhaust gas. In operation, the oxygen sensor produces an output signal which represents an electromotive force induced between the two electrodes according to the principle of an oxygen concentration cell. In recent years, there has been an increasing tendency to use an elongate planar sensing element rather than a conventionally used tubular sensing element, in view of ease of manufacture and structural simplicity of the sensor. Such an elongate planar sensing element has, at its one end, an oxygen detecting portion to be exposed to an exhaust gas or some other type of measurement gas. Such planar oxygen sensing elements and oxygen sensors incorporating a planar oxygen sensing element are disclosed, for example, in U.S. Pat. No. 4,450,065, and Japanese Patent Application laid open in 1983, under Publication No. 58-172542.

Oxygen sensors of various types as discussed above are installed such that the oxygen detecting portion of their oxygen sensing element is generally exposed to an exhaust gas or other measurement gas of an elevated temperature. Further, the sensing element is positively heated by a built-in electrical heater so as to maintain its detecting portion at a high temperature so that the detecting portion may function to effect accurate oxygen detection of the measurement gas. Thus, the entire portion of the sensing element is exposed to a relatively high temperature. Additionally, electrical leads for an electrical output indicative of the oxygen partial pressure of the measurement gas, and electrical leads for power supply to the electrical heater, are electrically connected to external conductors which extend from the oxygen sensor for electrical connection with external devices. The above-indicated exposure to heat of the sensing element results in difficulties and inconveniences in making electrical connections between the electrical leads of the sensing element and the external conductors.

For instance, the leads of the sensing element are electrically connected to connectors of a spring material such that the leads and the connectors are held in resiliently pressed contact with each other. These electrical connectors are electrically connected to suitable external conductor members. Such electrical connections by means of pressed contact of the leads with the connectors suffer a fatigue of the resilient connectors and oxidation of the contacts due to exposure to heat. An alternative method of electrical connection is available, wherein the external conductor members are brazed to terminals of the leads. This method, however, has problems that a brazing material such as Ag undergoes migration, and the brazed portion are likely to crack or flake off. In either case, the oxygen sensor of the type indicated above is not completely satisfactory in reliability of its electrical connections.

SUMMARY OF THE INVENTION

It is therefore an object of the present invention to provide an improved oxygen sensor which is free from the above-discussed inconveniences experienced in the prior art.

According to the invention, there is provided an oxygen sensor for determining an oxygen partial pressure of a measurement gas in a measurement-gas space, comprising: an elongate planar oxygen sensing element having an oxygen detecting portion adjacent to one longitudinal end thereof, and electrical terminal means adjacent to the other longitudinal end thereof; tubular protective means for accommodating and protecting the oxygen sensing element, the tubular protective means comprising first protective covering means for protecting at least an end portion of the sensing element which is located within the measurement-gas space and exposed to the measurement gas and which includes the oxygen detecting portion, the tubular protective means further comprising second protective covering means for covering the remaining portion of the sensing element which is not exposed to the measurement gas; and a retainer housing for attaching the tubular protective means to a partition wall defining the measurement-gas space, the elongate planar oxygen sensing element having a length of at least 40 mm as measured from the partition wall to the above-indicated other longitudinal end.

In the oxygen sensor of the present invention constructed as described above, the tubular protective means is positioned relative to the retainer housing and the sensing element is dimensioned and positioned relative to the tubular protective means, such that a length of the sensing element from the surface of the partition wall to the above-indicated other longitudinal end is not less than 40 mm, so that an end portion adjacent to said other longitudinal end of the sensing element is maintained below 200° C., and so that a variation in temperature of the end portion during operation and non-operation of the sensor may be minimized.

According to one advantageous embodiment of the invention, the tubular protective means is constituted by an integral or one-piece protective tubing member consisting of the first and second protective covering means. The protective tubing member is supported by the retainer housing with fluid tightness therebetween. Preferably, an air-tight sealing ring is interposed between the outer surface of the protective tubing member and the retainer housing so as to maintain fluid tightness therebetween. In this case, the protective tubing member may be securely fixed to the retainer housing with increased air tightness between the outer surface of the tubing member and the inner surface of the retainer housing.

According to another advantageous embodiment of the invention, the oxygen sensor further comprises at least one air-tight mass of an inorganic particulate material such as talc and alumina which fills a portion of a space defined between the periphery of the sensing element and the inner surface of the protective tubing member, over a predetermined length along the axis of the protective tubing member. This air-tight mass of inorganic particulate material permits the oxygen sensor to provide a high accuracy of detection of the oxygen concentration of the measurement gas for a prolonged period of time, even under severe operating conditions in which the sensor is subjected to repeated heating and cooling. In the case that the protective tubing member is secured to the retainer housing by means of an air-tight sealing ring as indicated above, it is desired that the air-tight mass in the protective tubing member be positioned opposite to the air-tight sealing ring via a wall of the protective tubing member, that is, positioned in alignment with the air-tight sealing ring in the longitudinal direction. In this instance, the air tightness of the air-tight mass may be improved during the assembly of the sensor.

In accordance with a further advantageous embodiment of the invention, the first protective covering means of the tubular protective means has at least one aperture for introducing therein the measurement gas. The at least one aperture is formed in a portion of a cylindrical wall of the first protective covering means which does not face the oxygen detecting portion of the sensing element. If necessary, the first protective covering means may have an opening at one end of its cylindrical wall on the side corresponding to the longitudinal end of the sensing element adjacent to which the oxygen detecting portion is disposed. In such cases wherein the tubular protective means has such a fluid-path means in the form of an aperture or an opening as indicated above, the measurement gas will not directly impinge upon the oxygen detecting portion, whereby the detecting portion is effectively protected from deterioration due to direct exposure to a stream of the measurement gas. Thus, the life expectancy of the oxygen sensor may be improved. Further, the formation of the fluid-path means in the selected portions of the tubular protective means contributes to eliminating the need for accurate circumferential positioning of the tubular protective means with respect to a flow of the measurement gas in order to avoid direct impingement of the measurement gas upon the oxygen detecting portion. In a preferred form of the present embodiment, the at least one aperture is formed in at least one part of the cylindrical wall of the first protective covering means which is opposite to at least one of opposite side surfaces of the sensing element, which side surfaces cooperate with opposite primary surfaces of the sensing element to define the periphery of the sensing element in transverse cross section thereof. Since the oxygen detecting portion is disposed on one of the opposite primary surfaces, the measurement gas introduced through the aperture will not directly impinge upon the oxygen detecting portion. It is possible that the fluid-path means consists solely of an opening which is formed at the end of the cylindrical wall of the first protective covering means on the side corresponding to the longitudinal end of the sensing element adjacent to which the oxygen detecting portion is disposed. The opening allows the measurement gas to flow into the first protective covering means.

For easy and fast electrical connection of the sensing element, with a simple coupling structure, during assembly of the sensor, it is preferred that the oxygen sensor comprises connector means which includes connectors disposed adjacent to the electrical terminal means. The terminal means is exposed on a surface of the planar sensing element and held in direct contact with the connectors of the connector means. In an advantageous form of the electrical connecting arrangement, the electrical terminal means takes the form of a plug, while the connector means takes the form of a receptacle in which the plug is inserted for pressed contact with the electrical terminal means.

The sensing element may incorporate an electrical heater to heat the oxygen detecting portion and hold the detecting portion at a suitable elevated temperature, in order to permit the oxygen detecting element to provide an electrical output which accurately represents the oxygen concentration of the measurement gas. In this case, the electrical terminal means may comprise electrical contacts for power supply to the electrical heater.

According to a preferred embodiment of the invention, the electrical terminal means includes electrical contacts which are raised above the surface of the planar sensing element, to insure connection of the contacts with the corresponding connectors.

The oxygen detecting portion of the sensing element may be made of a solid electrolyte material consisting substantially of zirconia ceramics, and is operated to determine the oxygen partial pressure of the measurement gas based on an electromotive force induced between electrodes disposed on the solid electrolyte. Alternatively, the oxygen detecting portion may be made of an oxide semiconductor the electrical resistance of which is varied as a function of the oxygen partial pressure of the measurement gas.

BRIEF DESCRIPTION OF THE DRAWING

These and other objects, and many of the attendant features and advantages of this invention will be readily appreciated as the same becomes better understood by reference to the following detailed description of illustrative embodiments when considered in connection with the accompanying drawings, in which.

DETAILED DESCRIPTION OF THE PREFERRED EMBODIMENTS

Figure 1:
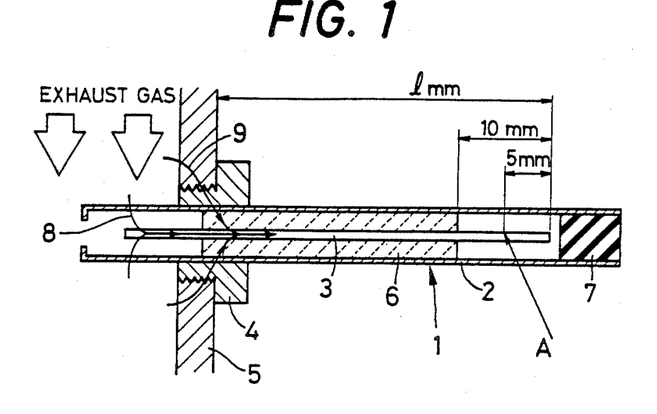
FIG. 1 is a cross sectional view of an oxygen sensor and a retainer housing for attaching the oxygen sensor to an exhaust pipe, used in experiments wherein a temperature of a sensing element of the sensor was measured at a portion adjacent to its longitudinal end on the side of an atmosphere, with various lengths of extension of the sensing element from the exhaust pipe.
Figure 2:
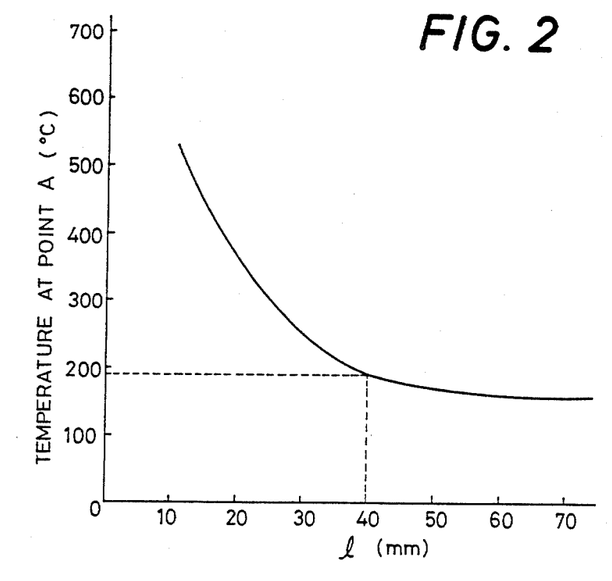
FIG. 2 is a graph showing measurements of the temperature of the sensing element in relation to the extension length of the sensing element.

FIG. 2 shows temperatures of an oxygen sensing element 3 of an oxygen sensor 1 installed in position as illustrated in FIG. 1, which temperatures were measured at a longitudinal end portion of the sensing element 3 remote from an exhaust gas.

More specifically, the oxygen sensor 1 was installed at an ordinary detecting position suitable for sensing an exhaust gas produced from an engine, that is, attached to an exhaust manifold or pipe 5 (partition wall separating the exhaust gas from the ambient atmosphere) of the engine, such that the sensing element 3 fixed within a protective tubing member 2 has a predetermined extension length l as measured from the outer surface of the exhaust pipe 5 up to a second longitudinal end on an ambient atmosphere side of the sensing element, as indicated in FIG. 1. The engine was operated to place the oxygen sensor 1 in the most severe conditions to which the sensor 1 is likely to be exposed. In other words, the engine was operated so that the oxygen sensor 1 was exposed to an exhaust gas of about 900° C. The sensing element 3 has a width of 4 mm, and a thickness of 1.2 mm, and incorporates an electrical heater of 3W capacity. The temperature was measured at point A adjacent to the second longitudinal end of the sensing element 3, with different values of the extension length l of the sensing element. Measurements of the temperature are shown in FIG. 2. In the oxygen sensor 1 used in the above experiment, the sensing element 3 is fixedly positioned within the protective tubing member 2 by a holder member 6, such that the holder member 6 fluid-tightly divides the interior of the protective tubing member 2 into two spaces on opposite sides of the holder member 6. The sensing element 3 has an oxygen detecting portion which is located adjacent to a first longitudinal end on the side of the exhaust gas, so that the detecting portion is exposed to the exhaust gas introduced through the corresponding end of the protective tubing member 2. The second longitudinal end on the side of the ambient atmosphere is closed by a rubber plug 7.

The temperature of the sensing element 3 at point A is raised by two factors of heat transfer from the exhaust gas to point A. The first factor is a transfer of heat (indicated at 8 in FIG. 1) to point A directly through the sensing element 3 itself, while the second factor (indicated at 9 in FIG. 1) is a transfer of heat via the exhaust pipe 5, and via a retainer housing 4 by which the sensor 1 is attached to the exhaust pipe 5. However, a rise in the temperature at point A is primarily caused by the latter factor of heat transfer (9). To restrain the temperature rise at point A of the sening element 3, the length l of the sensing element 3 between its first longitudinal end and the attaching surface of the exhaust pipe 5 is determined according to the principle of the invention, as described below.

As is apparent from the graph of FIG. 2, the temperature at point A of the sensing element 3 is held below 200° C. when the extension length l is not less than 40 mm. A decrease in this extension length l will cause an abrupt rise in the temperature at point A of the sensing element 3. With this fact taken into consideration, the sensing element 3 is dimensioned and positioned within the protective tubing member 2 such that a length of a portion of the sensing element 3 extending on the ambient atmosphere side of the sensing element, is at least 40 mm, more precisely, the second longitudinal end of the sensing element 3 is spaced away from the outer surface of the exhaust pipe 3 by a distance l of at least 40 mm.

To further clarify the present invention, preferred embodiments of the invention will be described in detail by reference to FIGS. 3-19 of the accompanying drawing.

Figure 3:
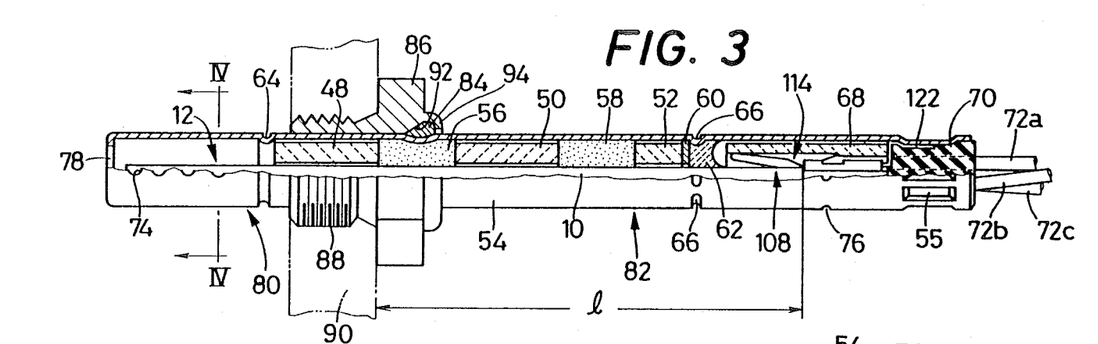
FIG. 3 is a partly cutaway view in longitudinal cross section of one embodiment of an oxygen sensor of the invention.

There is shown in FIG. 3 an oxygen sensor embodying the invention, which comprises an elongate planar oxygen sensing element of a laminar structure generally indicated by 10. The planar sensing element 2 is formed essentially of stabilized zirconia ceramics or other oxygen-ion conductive solid electrolyte materials. As illustrated in a transverse cross sectional view of FIG. 4 and in a perspective view of FIG. 5, the sensing element 10 is an elongate body having a rectangular shape in transverse cross section and having a small width relative to its length. The sensing element 10 has an oxygen detecting portion 12 at a first longidudinal end (i.e., the left hand side end in FIGS. 3 and 5). The oxygen detecting portion 12 produces an electrical signal according to the principle of an oxygen concentration cell. The electrical signal is fed to an external device through electrical connections at a second longitudinal end (right-hand side end in FIGS. 3 and 5) of the sensing element 10.

Described in greater detail referring to FIGS. 6-9, the sensing element 10 is a laminar structure consisting of many superposed layers. The laminar structure of the sensing element 10 comprises an elongate planar solid electrolyte body 14 made essentially of zirconia, and a porous inner electrode 16 of platinum, or any other suitable material, which is formed by printing on an area of the outer surface of the solid electrolyte body 14 adjacent to one end thereof corresponding to the first longitudinal end of the sensing element 10. On the surface of the solid electrolyte body 14 on which the inner electrode 16 is printed, there are laminated a U-shaped zirconia frame 18 and an oxygen sensing layer 20, which are also made essentially of zirconia ceramics, such that the inner electrode 16 is interposed between the solid electrolyte body 14 and the zirconia frame 18, and such that the sensing layer 20 is disposed on the zirconia frame 18. A porous outer electrode 22 made of the same material as the inner electrode 16 is printed on the sensing layer 20. The outer electrode 22 is protected, except at its sensing portion, by a protective layer 24 which is made of the same material as the sensing layer 20.

Figure 6:
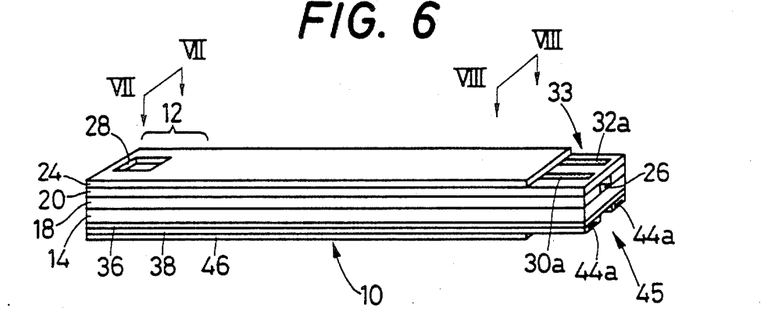
FIG. 6 is a perspective view of an example of the oxygen sensing element used in the oxygen sensor of FIG. 3.
Figure 7:
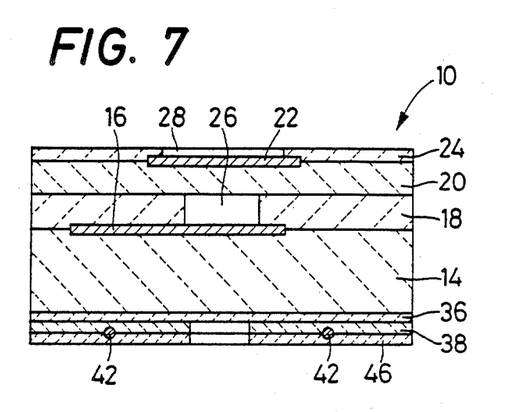
FIGS. 7 and 8 are cross sectional views taken along lines VII—VII and VIII—VIII of FIG. 6, respectively.
Figure 8:
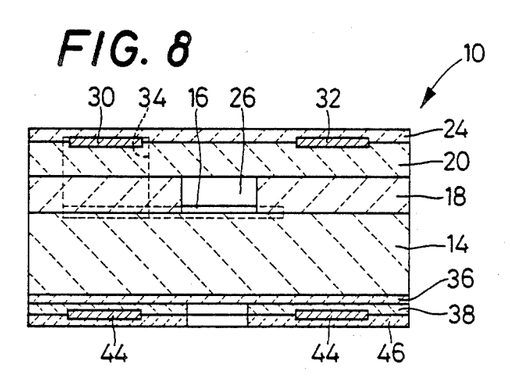
Figure 9:
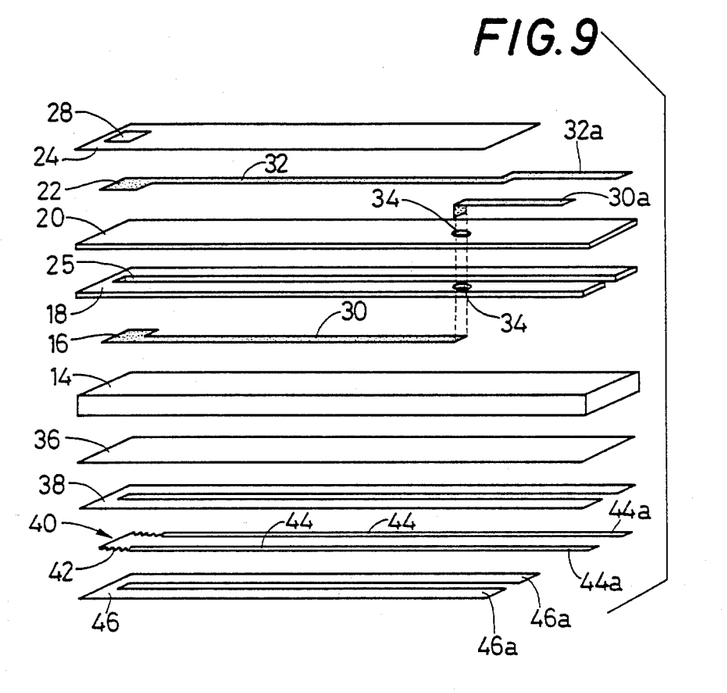
FIG. 9 is an exploded view of the oxygen sensing element of FIG. 6.

The zirconia frame 18 has an elongate rectangular cutout 25 formed along the length thereof. As shown in FIGS. 6–8, this cutout 25 cooperates with the solid electrolyte body 14 and the sensing layer 20 to define a reference-gas passage 26 which is closed at its one end near the end of the zirconia frame 18 corresponding to the first longitudinal end of the sensing element 10. The reference-gas passage 26 is open to ambient air at its other end corresponding to the second longitudinal end of the sensing element 10. The inner electrode 16 is disposed adjacent to the closed end part of the reference-gas passage 26 so that the electrode 16 is exposed to the atmosphere in the passage 26. Additionally, the outer electrode 22, which is formed on the side of the sensing layer 20 opposite to the zirconia frame 18, is located substantially in alignment with the inner electrode 16, so that the electrode 22 is exposed to a measurement gas (exhaust gas) outside the sensing element 10, via a window 28 formed in the protective layer 24. The inner and outer electrodes 16, 22 are provided with electrical leads 30, 32, respectively, which extend therefrom along the length of the sensing element 10 toward its outer or second longitudinal end, for electrical connection of the electrodes 16, 22. The entire length of the electrical lead 32 of the outer electrode 22 is formed on the outer surface of the sensing layer 20, while the electrical lead 30 of the inner electrode 16 is partially formed on the surface of the solid electrolyte body 14. Stated more particularly, the zirconia frame 18 and the sensing layer 20 have holes 34, 34 formed through the thickness thereof. The electrical lead 30 is turned, at its intermediate portion, at right angles to the surface of the solid electrolyte body 14 toward the electrical lead 32, so that its end portion 30a remote from the inner electrode 16 is disposed in substantially the same plane as the corresponding end portion 32a of the electrical lead 32 of the outer electrode 22. This plane is substantially perpendicular to the direction of thickness of the sensing element 10, as shown in FIG. 6. The electrical leads 30, 32 extend, in parallel with each other, from the respective electrodes 16, 22 between the sensing and protective layers 20, 24 toward the second longitudinal end of the sensing element 10 and are exposed at 30a, 32a, at the second end portion of the sensing element 10, as clearly shown in FIG. 6. These end portions 30a, 32a of the electrical leads 30, 32 serve as electrical contacts which constitute first electrical terminal means 33.

In the above-described arrangement of the oxygen sensing element 10, an external space communicating with the window 28 at the detecting portion 12 is kept in a fluid-tight condition with respect to the reference-gas space 26 defined by the zirconia frame 18, solid electrolyte body 14 and sensing layer 20. The inner electrode 16 is exposed to a reference gas, such as ambient air, in the passage 26, while the outer electrode 22 is exposed to the outside measurement gas introduced through the window 28. With these gases contacting the inner and outer electrodes 16, 22, an electromotive force is induced, according to the principle of an oxygen concentration cell, between the inner and outer electrodes 16, 22 due to a difference in oxygen partial pressure between the two different gases, whereby an output signal indicative of such an electromotive force is obtained through the respective electrical leads 30, 32.

In this illustrated embodiment, the ambient air is introduced as a reference gas into the reference-gas passage 26 through its open end at the second longitudinal end of the sensing element 10. Moreover, an exhaust gas emitted from an internal combustion engine such as an engine of an automotive vehicle, is introduced as a measurement gas, toward the outer electrode 22 through the window 28 at the detecting portion 12 of the sensing element 10. Namely, the oxygen concentration of the measurement gas in the form of an exhaust gas is measured by using ambient air as a reference gas. The electrical output signal representative of the oxygen concentration of the exhaust gas is obtained through the electrical leads 30, 32, at their end portions 30 at the first electrical terminal means 33.

On the side of the solid electrolyte body 14 opposite to the side on which the inner electrode 16 is printed, there are disposed an alumina insulating layer 36, a zirconia insulating layer 38, and an electrical heater layer 40 which comprises a heating element 42 and two electrical leads 44, 44 connected thereto. The heating element 42 is located in alignment with the oxygen detecting portion 12 of the sensing element 10. The electrical leads 44, 44 extend from the heating element 42 along the length of the sensing element 10 toward its second longitudinal end, so that the heating element is energized through these leads 44, 44 to heat the detecting portion 12 of the sensing elment 10. This pair of electrical leads 44, 44 are protected, except at their end portions 44a, 44a, by respected spaced-apart parallel portion 46a, 46a (FIG. 9) of a protective layer 46 made of zirconia ceramics, against exposure thereof to the exhaust gas. Stated differently, the end portions 44a, 44a are exposed at the second longitudinal end of the sensing element 10, and serve as electrical contacts which constitute second electrical terminal means 45 disposed on the side opposite to the first electrical terminal means 33 for the inner and outer electrodes 16, 22. The positive heating of the oxygen detecting portion 12 by the electrical heater 40 makes it possible to shorten the required warming-up time before the operation of the sensor stabilizes after the beginning of exposure of the detecting portion 12 to an exhaust gas from a cold engine. Further, the electrical heater 40 maintains the detecting portion 12 at a suitable operating temperature even while the temperature of the exhaust gas is not sufficiently high for intended operation of the sensor. Thus, the heater 40 enables the oxygen sensor to achieve stable and accurate measurement of the oxygen concentration of the measurement gas at any time.

The sensing element 10 is produced in a suitable known manner, for example by laminating on a green sheet layers of the electrodes and heater, and other layers such as insulating layers, and co-firing the multi-layer laminar structure. Alternatively, the sensing element 10 may be manufactured by forming the above indicated layers on the green sheet with a printing method, and co-firing the printed multi-layer structure. While the sensing element 10 is preferably made of a solid electrolyte material containing zirconia as a major component, it is possible to use other solid electrolyte materials for the sensing element 10.

Further, the oxygen detecting portion 12 of the sensing element 10 may be formed substantially of an oxide semiconductor such as titanium oxide whose electrical resistance is varied as a function of an oxygen concentration of an exhaust gas or other measurement gas. In this instance, the oxygen sensor detects a variation in the electrical resistance of the detecting portion 12 which is caused by a variation in the oxygen partial pressure of the measurement gas.

Figures 4, 5:
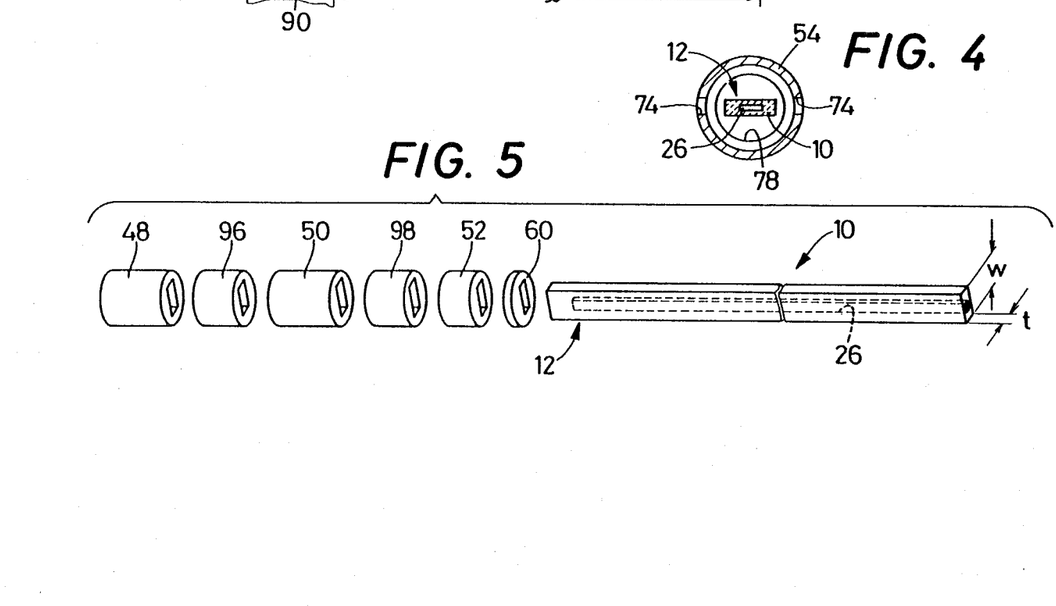
FIG. 4 is a transverse cross sectional view taken along line IV—IV of FIG. 3.
FIG. 5 is an exploded view of an oxygen sensing element and other parts of the oxygen sensor of FIG. 4, indicating the manner of assembling thereof.

Referring back to FIGS. 3-5, the elongate planar or plate-like sensing element 10 having the oxygen detecting portion 12 adjacent to its first longitudinal end is supported at three spaced-apart positions along its longitudinally intermediate portion, by a first, a second and a third ceramic insulating member 48, 50, 52 having a suitable length. These first, second and third ceramic insulating members 48, 50, 52 supporting the sensing element 10 are accommodated in a cylindrical protective tubing member 54 made of stainless steel or other suitable metallic materials. The three ceramic insulating members 48, 50, 52 and the sensing element 10 are fixed in the protective tubing member 54, by three fillers in the form of: a first air-tight mass 56 disposed between the first and second ceramic insulating members 48 and 50; a second air-tight mass 58 disposed between the second and third ceramic insulating members 50 and 52; and a bonding mass 62 provided adjacent to a washer 60 which is positioned in abutment on one end of the third air-tight mass 52 on the side of the second longitudinal end of the sensing element 10. Thus, the sensing element 10 is retained in alignment with the centerline of the protective tubing member 54, as shown in FIG. 4.

In the above arrangement, the sensing element 10 is accommodated and fixed in the protective tubing member 54 such that the detecting portion 12 adjacent to the first longitudinal end and the open end of the reference-gas passage 26 at the second longitudinal end are located respectively within spaces in opposite first and second opposite end portions of the protective tubing member 54 which are air-tightly separated from each other by the first and second air-tight masses 56, 58. The tubing member 54 is radially inwardly compressed at two longitudinal spaced-apart portions thereof to provide a first and a second radially inward protrusion 64, 66, as shown in FIG. 3. These inward protrusions 64, 66 prevent the first, second and third ceramic insulating members 48, 50, 52, the first and second air-tight masses 56, 58, and the washer 60 from moving in the tubing member 54 in the longitudinal direction.

A fourth ceramic insulating member 68 is positioned in the protective tubing member 54, such that the second longitudinal end portion of the sensing element 10 is inserted in an inner end portion of the insulating member 68. This fourth insulating member 68 is fixed in place such that the insulating member 68 is sandwiched by the second longitudinal end of the sensing element 10 and a rubber plug 70 which is press-fitted in the second end portion of the protective tubing member 54. Electrically conductive members in the form of lead wires 72a, 72b and 72c extend through the rubber plug 70 into the fourth ceramic insulating member 68. A plurality of connectors (which will be described referring to FIG. 13) are supported in the insulating member 68 and are electrically connected to the lead wires 72a, 72b and 72c, and to a ground 122. With these connectors, the lead wires 72a, 72b, 72c are connected to the electrical leads 30, and 44, 44 extending from the inner electrode 16 of the sensing element 10, and from the electrical heater 40. The electrical lead 32 extending from the outer electrode 22 is electrically connected to the protective tubing member 54 through the corresponding connector and the ground 122, so that the outer electrode 22 is grounded via a retainer housing 86 (which will be described) which supports the protective tubing member 54. In the above arrangement, an electromotive force between the inner and outer electrodes 16, 22 is obtained between the lead wire 72a and the ground 122, and the electrical heater 40 is powered through the lead wires 72b, 72c to heat the oxygen detecting portion 12, as previously described.

The rubber plug 70 closing the opening of the tubing member 54 at its second end prevents entry of a fluid such as water into the tubing member 54. Further, the second end portion of the protective tubing member 54 in which the rubber plug 70 is accommodated, is compressed or calked radially inwardly against the circumferential surface of the rubber plug 70. As a result, the second end portion of the tubing member 54 is provided with indented parts 55, as shown in FIG. 3, which effectively retain the rubber plug 70 in the tubing member 54. The inwardly compressed rubber plug 70 firmly holds the lead wires 72, 72b, 72c and thereby prevents vibrational or rattling movements of these lead wires which would otherwise be transmitted to the associated components within the oxygen sensor, particularly to the electrical connections. Namely, a radially inward compressive force imparted to the rubber plug 70 is effective to protect the electrical connections within the tubing member 54 from fatigue failure due to vibrations of the leads.

As shown in FIG. 3, the protective tubing member 54, accommodating therein the sensing element 10, a plurality of has apertures 74 in the first end portion, and air-inlet apertures 76 in its portion corresponding to the fourth ceramic insulating member 68. As described later, the oxygen sensor is installed such that the first longitudinal end of the protective tubing member 54 is located within a fluid conduit through which the measurement gas (exhaust gas) flows. In this condition, the measurement gas is introduced into the first longitudinal end of the tubing member 54 through the apertures 74, and is directed to the oxygen detecting portion 12 of the sensing element 10. Meanwhile, the ambient air is introduced through the air-inlet apertures 76 into the reference-gas passage 26 formed in the sensing element 10. More particularly described with reference to FIG. 4, the apertures 74 are formed in diameterially opposite parts of the cylindrical wall of the protective tubing member 54, such that the apertures 74 are opposite to opposite side surfaces of the sensing element 10 which are perpendicular to opposite primary surfaces which cooperate with the side surfaces to form a periphery of the sensing element 10 in transverse cross section of FIG. 4. The detecting portion 12 is disposed on one of the primary surfaces.

Since the apertures 74 are formed in the portions of the cylindrical wall of the protective tubing member 54 which do not face the primary surface of the sensing element 10 on which the detecting portion 12 is disposed, a stream of the measurement gas will not directly impinge upon the solid electrolyte and the outer electrode 22 at the detecting portion 12, whereby the deterioration of the detecting portion 12 may be effectively minimized and the service life of the sensor may be prolonged. The protective tubing member 54 is open at its first longitudinal end, i.e., the tubing member 54 is provided with an opening 78, which facilitates flows of the measurement gas within the tubing member 54, thereby improving a detecting response of the detecting portion 12 to a change in the oxygen concentration of the measurement gas.

It will be understood from the foregoing description that the protective tubing member 54 consists of a first protective covering portion 80 (between the first end and the first air-tight mass 56) which has the apertures 74, and a second protective covering portion 82 (between the first air-tight mass 56 and the second end). The first protective covering portion 80 protects a portion of the sensing element 10 which is exposed to the measurement gas and which includes the oxygen detecting portion 12. The second protective covering portion 82 protects the remaining portion of the sensing element 10. In other words, the integral or one-piece protective tubing member 54 constitutes tubular protective means which consists of first and second protective covering means 80 and 82. With the use of the one-piece protective tubing member 54, the overall construction of the oxygen sensor is simplified.

The one-piece protective tubing member 54 consisting of the first and second protective covering portions 80, 82 is inserted through the previously indicated retainer housing 86. The tubing member 54 is air-tightly fixed to the retainer housing 86 by means of an air-tight sealing ring 84 which is interposed between the outer surface of the protective tubing member 54 and the inner surface of the retainer housing 86. The protective tubing member 54 and the retainer housing 86 are so positioned relative to each other that the air-tight sealing ring 84 is aligned with the first air-tight mass 56 in the longitudinal direction of the tubing member 54. That is, the air-tight sealing ring 84 is positioned opposite to the first air-tight mass 56 via the wall of the tubing member 54. The retainer housing 86 is threaded to a wall of a fluid conduit, for example, to a partition wall 90 of an exhaust pipe of an automotive vehicle, such that the first protective covering portion 80 is located within the fluid conduit (in the exhaust pipe). Thus, the tubing member 54 is attached to the partition wall 90 with fluid tightness therebetween. With the tubing member 54 attached to the partition wall 90 by the retainer housing 86, the outer electrode 22 of the detecting portion 12 of the sensing element 10 in the tubing member 54 is exposed to the measurement gas (exhaust gas) which is introduced through the apertures 74 formed in the tubing member 54. At the same time, the inner electrode 16 is exposed to ambient air which is introduced through the apertures 76 and through the reference-gas passage 26. A difference in oxygen concentration between the measurement gas and the ambient air is detected as an electrical output represented by an electromotive force induced between the inner and outer electrodes 16, 22. The electrical output is obtained through the lead wire 72a and the earth lead 122.

Figures 10, 11A, 11B:
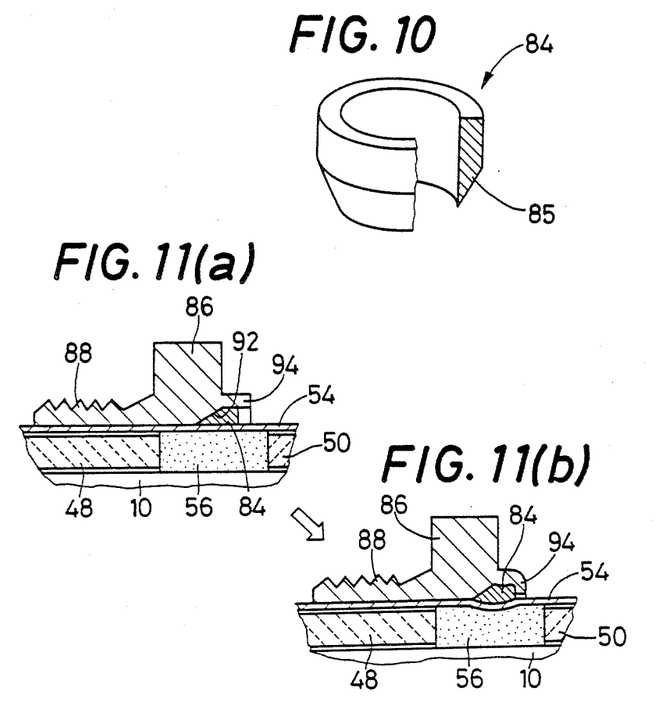
FIG. 10 is an perspective view of an air-tight sealing ring used in the oxygen sensor of FIG. 3.
FIG. 11(a) is a fragmentary view in cross section, showing a metallic retainer housing for supporting the oxygen sensor of FIG. 3 at its protective covering member, and related parts of the sensor, before the protective tubing member is finally secured to the metallic retainer housing.
FIG. 11(b) is a view similar to FIG. 11(a) after the protective tubing member has been finally secured to the metallic retainer housing.

As shown in enlargement in FIG. 10, the sealing ring 84 is a cylindrical member having a wedged end 85. On the other hand, the retainer housing 86 has an annular groove 92 in a rear part (on the side remote from the threaded part) of its inner surface defining a bore through which the tubing member 54 extends. This annular groove 92 and the outer surface of the tubing member 54 cooperate to define a sealing space which is filled by the sealing ring 84, such that its wedged end 85 is positioned on the inner side of the annular groove 92 longitudinally along the tubing member 54. The sealing ring 84 interposed between the retainer housing 86 and the tubing member 54 is retained within the sealing space (92) by calking the rear end of a cylindrical flange 94 of the retainer housing 86 against the outer end face of the sealing ring 84. By this calking action on the sealing ring 84, the inner wedged end 85 of the sealing ring 84 fills a gap between the inner surface of the retainer housing 86 and the outer surface of the tubing member 54, thereby maintaining air tightness between these two members 86, 54.

While the oxygen sensor is installed on the partition wall 90 defining the fluid conduit (measurement gas space in which the measurement gas exists), as described above, the sensing element 10 is positioned in the protective tubing member 54 such that a length l (FIG. 3) between the outer surface of the partition wall 90 and the second longitudinal end of the sensing element 10 is at least 40 mm. In other words, the partition wall 90, retainer housing 86, tubing member 54 and sensing element 10 are positioned relative to each other so that the length l of the sensing element 10, as measured from the partition wall 90, is not less than 40 mm. In this relative positioning, the temperature at the second longitudinal end of the sensing element 10 may be held below 200° C., that is, the first and second electrical terminal means 33, 45 for electrical connections of the sensing element 10 and the electrical heater 40 may be maintained at a sufficiently low temperature. Further, the positioning of the sensing element 10 with the length l of at least 40 mm contributes to reducing variations of the temperature of the sensing element 10 at its second longitudinal end during operating and non-operating times of the sensor. Accordingly, the sensing element 10 is protected against thermal stresses caused by a variation in the temperature.

It is desired that the overall length of the sensing element 10, particularly the length l between the partition wall 90 and the second longitudinal end, be determined to be as large as practicable, for holding the temperature at the second longitudinal end of the sensing element 10 as low as possible. However, the maximum length l is limited by the environments in which the oxygen sensor is installed. Usually, the upper limit of the length l is approximately 100 mm. The width and thickness of the planar sensing element 10 are determined suitably for obtaining an intended mechanical strength of the element 10, and in view of a degree of heat transfer through the element 10 from the first end toward the second end. Generally, the sensing element 10 has a width "w" within a range of 3–7 mm, and a thickness "t" within a range of 1–3 mm (FIG. 5). The mechanical strength of the sensing element 10 is lowered as the dimensions "w" and "t" are reduced. On the other hand, the amount of heat to be transferred through the sensing element 10 is increased and the temperature at its second end tends to be raised as the dimensions "w" and "t" are increased.

The two air-tight masses 56, 58 used in the illustrated embodiment are press-formed by compression of particles of from heat-resistant inorganic materials such as talc and alumina, while the bonding mass 62 is formed of a suitable inorganic bonding agent such as glass. The use of inorganic particulate material with a high heat-resistance (not lower than 500° C. in general, but depending upon operating environments of the sensor) permits the air-tight masses 56, 58 to maintain the intended air tightness for a relatively longer period of time even if the air-tight masses 56, 58 are cyclically heated and cooled. Similarly, the use of an inorganic bonding agent for the bonding mass 62 assures stable support and fixation of the sensing element 10 within the tubing member 54. In the present embodiment, one of the two air-tight masses, (i.e., air-tight mass 58 between the second and third ceramic insulating members 50, 52), also functions as a bonding mass similar to the bonding mass 62, to secure the sensing element 10 to the tubing member 54.

The first and second air-tight masses 56, 58 are formed during the assembly of the sensing element 10 and the related components. Stated in detail, the first, second, and third ceramic insulating members 48, 50, 52, washer 60, and press-molded articles 96, 98, are prepared as shown in FIG. 5. The articles 96, 98 which eventually serve as the first and second air-tight masses 56, 58, are press-molded from particles of talc or any other suitable inorganic material. Also, the tubing member 54 is prepared with only the first inward protrusion 64, viz., without the second inward protrusion 66 which is subsequently formed.

The sensing element 10 is passed through the insulating member 48, press-molded article 96, second insulating member 50, press-molded article 98, third ceramic insulating member 52, and washer 60, in the order of description. Subsequently, the assembly of the sensing element 10, with the above-indicated components, is inserted into the protective tubing member 54 through the opening at the second longitudinal end, while the tubing member 54 is supported in its upright posture with a suitable fixture, such that the second end is open upward. The inserted assembly is stopped and positioned by the first inward protrusion 64 when the lower edge of the first insulating member 48 is brought into abutment with the protrusion 64. At the same time, the sensing element 10 is positioned by the fixture supporting the tubing member 54.

In this condition, the washer 60 is pressed against the upper end face of the third insulating member 52, with a suitable tool, whereby the low-density press-molded articles 96, 98 are further compressed and deformed or shaped into the air-tight masses 56, 58 having an increased density. Thus, the air-tight masses 56, 58 fill the space defined by the tubing member 54, sensing element 10, and first, second and third insulating members 48, 50, 52. With the pressure exerted on the washer 60, the tubing member 54 is radially inwardly compressed to form the second inward protrusion 66 which holds the inserted assembly in position.

After the sensing element 10 has been positioned and fixed in the tubing member 54, and the air-tight masses 56, 58 have been formed, a suitably pre-formed mass of glass is inserted into the tubing member 54 and fused into the bonding mass 62.

The retainer housing 86 is mounted on the protective tubing member 54, so that the retainer housing 86 is positioned longitudinally of the tubing member 54 so as to substantially cover a portion of the latter in which the first air-tight mass 56 is disposed. Described more specifically referring to FIGS. 11(a) and 11(b), the cylindrical flange 94 of the retainer housing 86 is calked against the sealing ring 84 positioned in the sealing space (annular groove) 92, whereby the retainer housing 86 is secured to the tubing member 54. The calking action on the cylindrical flange 94 causes the sealing ring 84 to force the corresponding part of the cylindrical wall of the tubing member 54 radially inwardly against the first air-tight mass 56, and consequently causes that part of the wall to be inwardly protruded. Since the volume of the space accommodating the air-tight mass 56 is fixed by the defining surfaces of the first and second insulating members 48, 50, tubing member 54 and sensing element 10, the inward protrusion of the cylindrical wall of the tubing member 54 results in further compression of the particles of the air-tight mass 56 and accordingly increases the density or air tightness of the air-tight mass 56. In addition, the reaction force of the first air-tight mass 56 acts to increase the surface pressure between the tubing member 54 and the sealing ring 84, and therefore improve the air-tightness between the tubing member 54 and the retainer housing 86.

The protective tubing member 54 used in this embodiment is made of stainless steel SUS-310S having an average coefficient of thermal expansion of $17.5 \times 10^{-6}$ °C.$^{-1}$ at 0°–600° C. The retainer housing 86 and the sealing ring 84 are made of stainless steel SUS-304 with an average coefficient of thermal expansion of $18.9 \times 10^{-6}$ °C.$^{-1}$ at 0°–600° C. As indicated above, the difference in thermal expansion coefficient between any two of the three members 54, 86, 84 is selected to be relatively small for increased air tightness between the retainer housing 86 and the tubing member 54. In other words, the use of materials whose thermal expansion coefficients differ from each other in a large degree would cause a relatively large gap to be present between the retainer housing 86 and the tubing member 54 after a long period of service of the oxygen sensor under varying temperatures. For improved air tightness between the retainer housing 86 and the tubing member 54, it is recommended to use metallic materials whose difference in thermal expansion coefficient is not greater than $3 \times 10^{-6}$ ° C.$^{-1}$.

Figure 12:
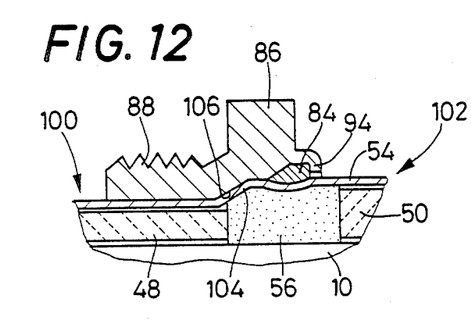
FIG. 12 is a fragmentary cross sectional view corresponding to FIG. 11(b), showing another embodiment of the invention.

While the protective tubing member 54 has the same diameter over the entire length, it should be appreciated that the tubing member 54 can be formed from a two-diameter pipe, as depicted in FIG. 12, which has a small-diameter end portion 100 (corresponding to the first protective covering portion 80 of FIG. 3), a large-diameter portion 102 (corresponding to the second protective covering portion 82 of FIG. 1), and a tapered portion 104 connecting the portions 100, 102. In this case, the protective tubing member 54 is easily and suitably clamped by a fixture when the press-molded article 96 in the tubing member 54 is compressed into the first air-tight mass 56 during the assembly of the oxygen sensor. In other words, the use of such a two-diameter pipe makes it possible to avoid buckling or other troubles with the tubing member 54, which would take place if the tubing member 54 is clamped at its end portion during the assembly of the sensor. Further, the two-diameter pipe permits its tapered portion 104 to snugly fit the mating inner surface 106 of the retainer housing 86, thereby assuring better air-tight sealing between the two members 54 and 86.

Figure 13:
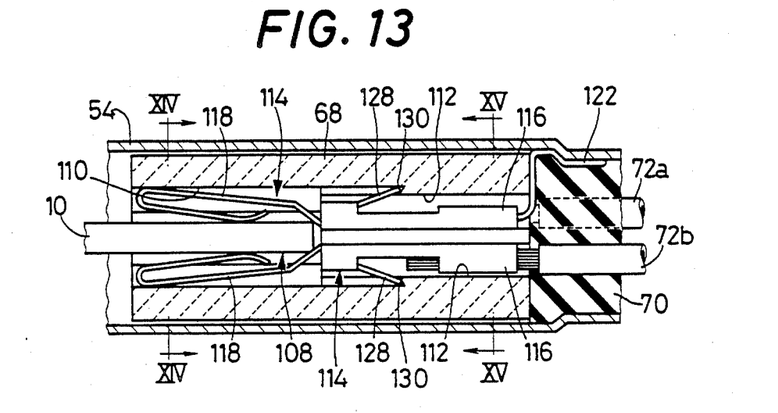
FIG. 13 is a fragmentary enlarged view in cross section (taken along line XIII—XIII of FIG. 14) of a portion of the oxygen sensor of FIG. 3, illustrating a ceramic insulator in which electrical connections of the sensing element are made.

The electrical leads 30, 32 of the electrodes 16, 22 and the electrical leads 44, 44 of the electrical heater 40 are electrically connected to the lead wires 72a, 72b, 72c and the earth lead 122, as indicated in FIG. 13 and the subsequent figures.

Figure 14:
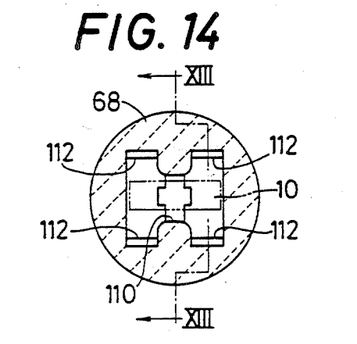
FIGS. 14 and 15 are views in cross section taken along lines XIV—XIV and XV—XV of FIG. 13, respectively.
Figure 15:
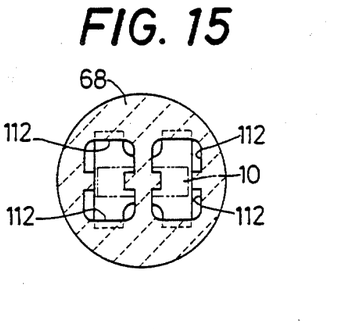

More specifically as described by reference to FIGS. 13-15, the fourth ceramic insulating member 68 is a generally cylindrical member which has, on one side thereof, a recess 110 in which there is inserted an electrical plug portion 108 of the sensing element 10 that carries the first and second electrical terminal means 33, 45. As most clearly shown in FIG. 13, the fourth ceramic insulating member 68 further has, on the other side, four lead-wire holes 112 into which the end portions of the lead wires 72a, 72b, 72c and ground 122 are inserted. These four lead-wire holes 112 are disposed such that the extension lines of the two holes 112 are aligned with the end portions 30a, 32a of the leads 30, 32, and those of the remaining two holes 112 are aligned with the end portions 44a, 44a of the leads 44, 44 on the opposite side of the sensing element 10. The four lead-wire holes 112 communicate with the recess 110 so that the lead wires 72a, 72b, 72c and earth lead 122 may be electrically coupled to the respective end portions (electrical contacts) 30a, 32a, 44a, 44a of the leads 30, 32, 44, 44 in a manner which will be described in detail.

Figure 16:
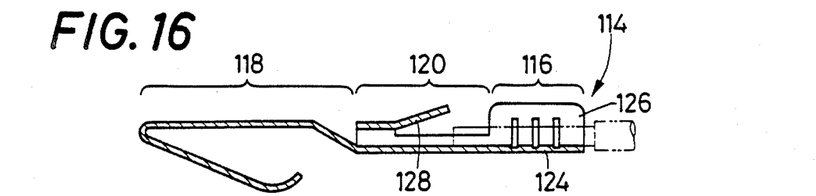
FIG. 16 is a front elevational view in cross section (taken along line XVI—XVI of FIG. 17) of an electrical connector used in the oxygen sensor of FIG. 3.
Figure 17:
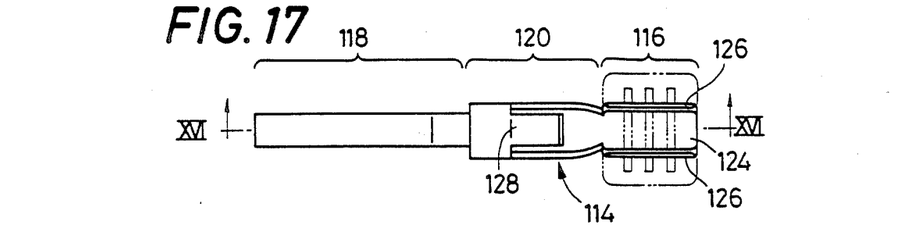
FIG. 17 is a plan view of the electrical connector of FIG. 16.
Figures 18, 19:
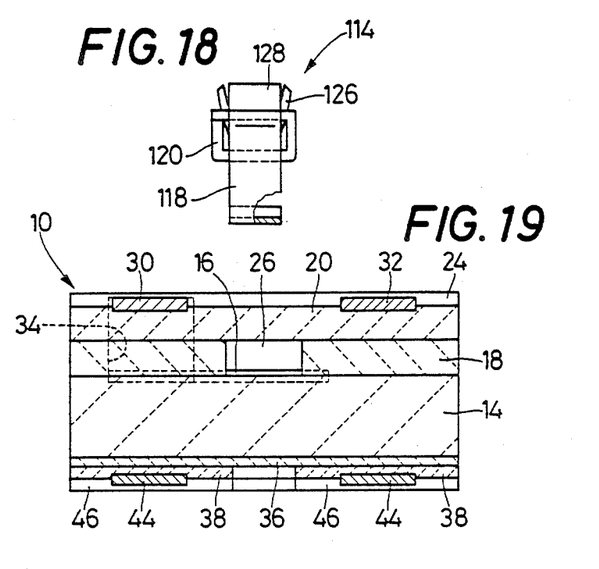
FIG. 18 is a partially cutaway left-hand side end view of the electrical connector of FIG. 16.
FIG. 19 is a view similar to FIG. 8, showing an alternative form of an electrical terminal portion of the sensing element at which electrical leads are exposed at their end portions.

Each of the lead wires 72a, 72b, 72c and ground 122 is provided at its end with the previously indicated connector 114, which is made of a spring or resilient material. As illustrated in FIGS. 16-18, each connector 114 consists of: a fixing portion 116 having a U-shaped transverse cross section before it is calked or crimped to grip the corresponding lead wire 72a, 72b, 72c or ground 122; a spring portion 118 bent in V shape; and a generally tubular latching portion 120 connecting the fixing and spring portions 116, 118. The U-shaped fixing portion 116 is calked so as to grip the end portion of the lead wire 72a, 72b, 72c or ground 122, whereby the connector 114 is fixed to the lead wire or earth lead. The fixing portion 116 is provided with a pair of opposed sections 126, 126 which cooperate with a connecting portion 124 extending from the latching portion 120, to form a U-shaped structure. The opposed sections 126, 126 are bent inwardly into a U-shaped structure. Thus, the end portion of the lead wire 72a, 72b, 72c or ground 122 inserted in the U-shaped structure is electrically connected to the connector 114.

The latching portion 120 has a latching lug 128 on one of its surfaces which is opposite to the connecting portion 124. The latching lug 128 is bent obliquely at a suitable angle with respect to the direction of length of the connector 114, so as to extend from its fixed end toward its free end on the side of the fixing portion 116, such that the free end is located away from the latching portion 120.

As shown in FIG. 13, the connector 114 is inserted through the respective lead-wire hole 112, and is positioned within the recess 110 such that the free end portion of the spring portion 118 is held in contact with the electrical plug portion 108 of the sensing element 10 located within the recess 118. More precisely stated, the free end of the spring portion 118 of the connectors 114 is held in resiliently pressed contact with the corresponding end portion 30a, 32a, 44a, 44a of the electrical lead 30, 32, 44, 44 which is exposed on the opposite surfaces of the electrical plug portion 108 (first and second electrical terminal means 33, 45) of the sensing element 10.

As described above, the electrical leads 30 and 32 on the first electrical terminal means 33, and the electrical leads 44 and 44 on the second electrical terminal means 45, are electrically connected to the ground 122, and the lead wires 72a, 72b, 72c, respectively. With the electrical connections by means of the connectors 114, an electromotive force representative of the oxygen concentration of the measurement gas is obtained between the earth lead 122 and the lead wire 72a, and the the electrical heater 40 built in the sensing element 10 to heat the element 10 is energized by application of power through the lead wires 72b and 72c.

Each connector 114 is positioned within the fourth ceramic insulating member 68 such that the latching lug 128 of the latching portion 120 is held in abutting contact with a shoulder 130 formed adjacent to the lead-wire hole 112, as shown in FIG. 13, whereby the connector 114 once inserted into the fourth ceramic insulating member 68 can not be moved away from the sensing element 10 (i.e., in the right direction as viewed in FIG. 13).

In the oxygen sensor arrangement described hitherto, the electrical connections of the connectors 114 to the lead wires 72a-72c and ground 122 may be accomplished simply by calking or crimping the fixing portion 116 of the connectors 114 on the end portion of the corresponding lead wire or earth lead. To make electrical connections of the connectors 114 to the electrical leads 30, 32, 44, 44 on the sensing element 10, the connectors 114 fixed to the lead wires 72a-72c and earth lead 122 are first inserted into the corresponding lead-wire holes 112 in the fourth ceramic insulating member 68 so that the spring portions 118 of the connectors 114 are positioned within the recess 110 so as to form a receptacle. Then, the insulating member 68 with the connectors 114 positioned therein is inserted into the second end portion of the protective tubing member 54 so that the electrical plug portion 108 of the sensing element 10 already positioned in the protective tubing member 54 is inserted into the receptacle formed by the connectors 114 in the recess 110 in the insulating member 68.

With the insulating member 68 thus inserted into the protective tubing member 54, the free ends of the spring portions 118 of the connectors 114 are held in resiliently pressed contact with the end portions 30a, 32a, 44a, 44a of the respective electrical leads 30, 32, 44, 44 which are exposed on the first and second electrical terminal means 33, 45 at the electrical plug portion 108 of the sensing element 10. Thus, the electrical connections of the electrical leads 30, 32, 44, 44 are effected to allow the sensing element 10 to provide an output of an electromotive force representative of the oxygen concentration of the measurement gas, and to permit the electrical heater 40 to be energized.

As is apparent from the foregoing detailed description, the electrical plug portion 108 of the sensing element 10 serves as a plug, while the spring portions 118 of the connectors 114 inserted into the fourth ceramic insulating member 68 serve as a receptacle which accommodates the plug for electrical connection therebetween. Hence, the mere coupling of the plug and the receptacle is sufficient to make electrical connections of the electrical leads 30, 32, 44, 44 of the sensing element 10 and the ground 122 and lead wires 72a, 72b, 72c. Namely, the first and second electrical terminal means 33, 45 at the electrical plug portion 108 constitute male connectors or contacts, while the connectors 114 constitute female connectors or contacts. The insulating member 68 serves as a housing for supporting the connectors 114 in the form of a receptacle resiliently engageable with the electrical plug portion 108.

Although the illustrated embodiment uses a plug in the form of the first and second electrical terminal means 33, 45 (electrical terminal portion 108), and a receptacle in the form of the connectors 114 supported in the insulating member 68, it is possible to construct the first and second terminal means 33, 45 in the form of a receptacle consisting of female electrical contacts, and to provide a plug consisting of male connectors (114) within the insulating member 68, so that the male connectors are inserted into the receptacle for electrical connection of the sensing element 10.

In the illustrated embodiment, wherein the electrical plug portion 108 of the sensing element 10 serves as a plug, it is preferred that the exposed end portions 30a, 32a, 44a, 44a of the electrical leads are formed so as to be raised or protruded above the surfaces of the sensing layer 20 and the zirconia insulating layer 38, as illustrated in FIG. 19. This arrangement assures sound contact of the exposed end portions 30a, 32a, 44a, 44a of the leads with the spring portions 118 of the connectors 114, even if the sensing element 10 is deflected, flexed or deformed in the direction of width thereof.

While each of the first and second electrical terminal means 33, 45 of the illustrated embodiment consists of the raised end portions 30a, 32a of the electrical leads 30, 32, or of the raised end portions 44a, 44a of the electrical leads 44, 44, it is possible that the first and second electrical terminal means 33, 45 may be constituted by end portions of the leads 30, 32, 44, 44, and base layers of a suitable thickness which are formed on the sensing layer 20 and the zirconia insulating layer 38 in order to serve as substrates for the end portions of the leads are formed.

The advantage of easy electrical connection of the sensing element 10 by means of direct contact of the electrical plug portion 108 with the connectors 114, is high geared with another advantage of the present oxygen sensor that the sensing element 10 is adapted such that the second longitudinal end is located at least 40 mm away from the outer surface of the partition wall 90 to which the protective tubing member 54 is attached by means of the retainer housing 86. Namely, the length l of at least 40 mm of the sensing element 10 as measured from the partition wall 90 to the second longitudinal end, makes it possible to maintain the temperature at the electrical plug portion 108 of the sensing element 10 below 200° C., thereby effectively minimizing the possibilities of fatigue of the spring portion 118 of the connectors 114, and oxidation of the end portions of the electrical leads. Consequently, the connectors 114 may be made of an ordinary spring material such as stainless steel, that is, there is no need of using a spring material having a specially high heat resistance. Thus, the present oxygen sensor is significantly improved in reliability of electrical connection, as well as in material cost of the connectors.

It will be obvious that the male-female or plug-receptacle connection between the electrical leads of the sensing element 10 and the external conductor members (lead wires and earth lead) may be replaced by another method of connection wherein the electrical leads of the sensing element 10 are brazed to the respective conductor members directly or by means of suitable connectors. In this instance, too, the minimum requirement of the length l of the sensing element 10 is conducive to prevention of otherwise possible Ag migration of a brazing material, cracking or removal of the brazed portions. Thus, the reliability of the electrical connection is improved.

While the present invention has been described in its preferred embodiments for illustrative purposes only, it is to be understood that the invention is not limited to the details of the illustrated embodiments, but may be embodied with various changes, modifications and improvements which may occur to those skilled in the art.

In the illustrated embodiment of FIG. 3, the first protective covering means 80 and the second protective covering means 82 which constitute tubular protective means for the sensing element 10 are formed by a unitary member in the form of the one-piece protective tubing member 54 of simple configuration and structure. While the use of such a one-piece tubing member permits easier manufacture of the tubular protective means, and simpler assembling of the oxygen sensor, than the use of two separate members for the first and second protective covering portions 80, 82 of the tubular protective means. However, it is possible that the first and second protective portions 80 and 82 are formed by separate tubular members, respectively.

While the air-tight masses 56, 58 for air-tightly retaining the sensing element 10 in the protective tubing member 54 are preferably made of particles of talc, other heat-resistant inorganic particulate materials, such as particles of alumina, may be used. Although the two air-tight masses are provided in the illustrated embodiment, it is possible that a single air-tight mass is provided, or three or more air-tight masses are provided at positions which are spaced apart from each other in the longitudinal direction along the sensing element 10. Further, the bonding mass 62 may be formed of from inorganic materials such as a cement, other than a glass as used in the illustrated embodiment. It is possible that such a bonding mass of inorganic materials is provided at two or more positions in the longitudinal direction of the sensing element 10.

Although the illustrated embodiment uses the airtight sealing ring 84 with a wedged end to secure the retainer housing 86 to the protective tubing member 54 with air tightness therebetween, the retainer housing 86 may be fixed to the tubing member 54 by means of welding or a press fit.

While the first protective covering portions 80 of the protective tubing member 54 has the apertures 74 and the opening 78 for introducing the measurement gas, it is possible to eliminate the apertures 74 so that the measurement gas is introduced solely through the opening 78. In this case, an improvement in the durability of the sensor may be expected.

It will be understood from the foregoing description that the oxygen sensor according to the invention is characterized in that its sensing element has a length of at least 40 mm as measured from the surface of partition wall to which the retainer housing is attached, up to the longitudinal end of the sensing element on the side remote from the measurement gas. This arrangement enables the portion of the sensing element adjacent to the second longitudinal end to be maintained at a relatively low temperature, whereby the electrical terminal portions for electrical connections for an electrical output of the sensor and for power supply to the heater may be held at a sufficiently low temperature. Thus, the reliability of the electrical connection of the sensor is improved. The sensor is suitably used as an exhaust gas sensor, and finds its industrial significance, particularly in the field of controlling an air-fuel ratio of an air-fuel mixture for an internal combustion engine.

What is claimed is:

1. An oxygen sensor for determining an oxygen partial pressure for a measurement gas in a measurement-gas space, comprising:

an elongate planar oxygen sensing element with an outer peripheral portion, having an oxygen detecting portion adjacent to a first longitudinal end thereof, and electrical terminal means adjacent to a second longitudinal end thereof, said electrical terminal means comprises a plug including at least one pair of electrical contacts which are exposed on a surface of said planar oxygen sensing element;

connector means disposed adjacent to said electrical terminal means, said connector means including electrical connectors which are held in direct electrical contact with said electrical terminal means, said electrical connectors comprising a resilient material and being held in a resilient pressed electrical contact with said at least one pair of electrical contacts of the electrical terminal means;

tubular protective means having an inner surface and an outer surface for accommodating and protecting said oxygen sensing element therein, said tubular protective means comprising a first protective covering portion for protecting at least an end portion of said sensing elment which is located within said measurement-gas space and exposed to said measurement gas and which includes said oxygen detecting portion, said tubular protective means further comprising a second protective covering portion covering a remaining portion of said sensing element which is not exposed to said measurement gas;

a retainer housing for attaching said tubular protective means to a partition wall defining said measurementgas space, said elongate planar oxygen sensing element having a length of at least 40 mm as measured from said partition wall to said second longitudinal end; and at least two air-tight masses of an inorganic particulate material which fill in at least portions of a space defined between the outer peripheral portion of the oxygen sensing element and the inner surface of the tubular protective means, said at least two air-tight masses being spaced apart from each other along a longitudinal axis of the tubular protective means, one of said at least two air-tight masses being located adjacent to said retainer housing and a second one of said at least two air-tight masses being located between said electrical terminal means and said one air-tight mass.

2. The oxygen sensor of claim 1, wherein said first and second protective covering portions are included in an integral protective tubing member, said integral protective tubing member being supported by said retainer housing with a fluid tightness therebetween.

3. The oxygen sensor of claim 2, further comprising an air-tight sealing ring located between the outer surface of said protective tubing member and said retainer housing so as to maintain fluid tightness therebetween.

4. The oxygen sensor of claim 2, wherein said tubular protective means comprises a pipe having a small-diameter portion and a large-diameter portion, said large diameter portion being larger in diameter than said small-diameter portion.

5. The oxygen sensor of claim 1, further comprising an air-tight sealing ring located between the outer surface of said protective tubing member and said retainer housing so as to maintain fluid tightness therebetween, and wherein said one of said at least two air-tight masses in said protective tubing member is positioned opposite to said air-tight sealing ring via a wall of said protective tubing member.

6. The oxygen sensor of claim 1, wherein said sensing element is fixed within said tubular protective means with a bonding agent selected from the group of inorganic materials consisting of cement and glass.

7. The oxygen sensor of claim 1, wherein said first protective covering means of the tubular protective means includes at least one aperture for introducing therein said measurement gas, said at least one aperture being formed in a portion of a cylindrical wall of the first protective covering means which does not face said oxygen detecting portion.

8. The oxygen sensor of claim 7, wherein said first protective covering means includes an opening at one end of its cylindrical wall on a side corresponding to said first longitudinal end of the sensing element.

9. The oxygen sensor of claim 7, wherein said elongate planar oxygen sensing element has opposite primary surfaces and opposite side surfaces which cooperate to form said outer peripheral portion of the sensing element in transverse cross section, said detecting portion being disposed on one of said opposite primary surfaces, said at least one aperture being formed in at least a portion of the cylindrical wall of the first protective covering means which is opposite to at least one of said opposite side surfaces of the sensing element.

10. The oxygen sensor of claim 1, wherein said first protective covering means includes an opening at one end thereof on a side corresponding to said first longitudinal end of the sensing element, said opening permitting said measurement gas to flow into said first protective covering means.

11. The oxygen sensor of claim 1, wherein said electrical terminal means comprises an output signal contact and a ground contact, and said tubular protective means comprises a metallic member, said ground contact being electrically connected to said second protective covering means through the corresponding one of said connectors.

12. The oxygen sensor of claim 1, wherein said electrical terminal means includes electrical contacts which are raised above the surface of the planar sensing element.

13. The oxygen sensor of claim 1, further comprising a rubber plug press-fitted into a longitudinal end portion of said second protective covering means, said connectors being electrically connected to respective conductor members which extend through said rubber plug for connection with an external device, a portion of said second protective covering means corresponding to said rubber plug being radially inwardly compressed to fluid-tightly hold said rubber plug and said conductor members.

14. The oxygen sensor of claim 13, wherein said sensing element comprises an electrical heater which is inclined to heat said oxygen detecting portion of said sensing element.

15. The oxygen sensor of claim 1, wherein said sensing element comprises an electrical heater which is included to heat said oxygen detecting portion of said sensing element, said electrical terminal means comprising electrical contacts for power supply to said electrical heater.

16. The oxygen sensor of claim 1, wherein said elongate planar oxygen sensing element is not longer than 100 mm and has a width of 3-7 mm, and a thickness of 1-3 mm, such that said second longitudinal end thereof does not exceed approximately 200° C. during operation of the oxygen sensor.

* * * * *